United States Patent [19]
Jaeger et al.

[11] Patent Number: 5,411,739
[45] Date of Patent: May 2, 1995

[54] APPARATUS FOR THE CONTROLLED DELIVERY OF NICOTINE, PROCESS FOR THE PRODUCTION THEREOF AND USE THEREOF

[75] Inventors: Halvor Jaeger, New-Ulm; Hans-Ranier Hoffmann, Neuwied; Reinhold Meconi, Neuwied; Robert-Peter Klein, Neuwied, all of Germany

[73] Assignee: LTS Lohmann Therapie-Systeme GmbH & Co. KG, Neuwied, Germany

[21] Appl. No.: 237,322

[22] Filed: May 3, 1994

Related U.S. Application Data

[63] Continuation of Ser. No. 974,682, Nov. 12, 1992, abandoned, which is a continuation of Ser. No. 566,855, Aug. 10, 1990, abandoned, which is a continuation of Ser. No. 353,672, filed as PCT/DE88/00479, Aug. 3, 1988, published as WO 89/01789, Mar. 9, 1989, abandoned.

[30] Foreign Application Priority Data

Sep. 1, 1987 [DE] Germany ............... 37 29 165.3
Dec. 23, 1987 [DE] Germany ............... 37 43 947.2

[51] Int. Cl.⁶ .................... A61F 13/02; A61L 15/16
[52] U.S. Cl. ........................ 424/448; 424/405; 424/449
[58] Field of Search ............... 424/448, 449, 405

[56] References Cited

U.S. PATENT DOCUMENTS

| | | | |
|---|---|---|---|
| 4,455,146 | 6/1984 | Noda et al. | 424/448 |
| 4,485,087 | 11/1984 | Otsuka et al. | 424/449 |
| 4,515,909 | 5/1985 | Sawano et al. | 428/36.92 |
| 4,564,364 | 1/1986 | Zaffaroni et al. | 424/484 |
| 4,597,961 | 7/1986 | Etscorn | 424/448 |
| 4,668,232 | 5/1987 | Cordes et al. | 424/448 |
| 4,714,655 | 12/1987 | Bordoloni et al. | 428/345 |
| 4,758,434 | 7/1988 | Kydonieus et al. | 424/449 |
| 4,769,028 | 9/1988 | Hoffmann et al. | 424/443 |
| 4,840,796 | 6/1989 | Sweet et al. | 424/448 |

FOREIGN PATENT DOCUMENTS

| | | |
|---|---|---|
| 0086468 | 8/1983 | European Pat. Off. |
| 0127282 | 12/1984 | European Pat. Off. |
| 0144486 | 6/1985 | European Pat. Off. |
| 0186019 | 7/1986 | European Pat. Off. |
| 3007368 | 4/1979 | Germany |
| 3438284AT | 7/1985 | Germany |
| 606885 | 8/1986 | Germany |
| 3629304 | 8/1986 | Germany |
| 58-189112 | 11/1983 | Japan |
| 8801516 | 3/1988 | WIPO |

*Primary Examiner*—Thurman K. Page
*Assistant Examiner*—William E. Benston, Jr.
*Attorney, Agent, or Firm*—Kalish & Gilster

[57] ABSTRACT

The invention relates to an apparatus for the controlled delivery of nicotine with a contact adhesive nicotine reservoir with uniform or irregular distribution of the nicotine, characterized in that the reservoir is produced using a hot melt contact adhesive with a processing temperature of 40° to 80°, preferably 40° to 60° and in particularly preferred manner 40° to 55° C., a process for the production thereof and the use of the apparatus in human or veterinary medicine, particularly for stopping people smoking, or as a respiratory, contact or stomach poison in pest control.

29 Claims, 1 Drawing Sheet

APPARATUS FOR THE CONTROLLED DELIVERY OF NICOTINE, PROCESS FOR THE PRODUCTION THEREOF AND USE THEREOF

This application is a continuation of application Ser. No. 07/974,682 filed Nov. 12, 1992, now abandoned May 3, 1994, which is a continuation of application Ser. No. 07/566,855, filed Aug. 10, 1990, now abandoned, which is a continuation of Ser. No. 07/353,672, filed as PCT/DE88/00479, Aug. 3, 1988, published as WO 89/01789, Mar. 9, 1989, and now abandoned.

BACKGROUND AND SUMMARY OF THE INVENTION

The invention relates to an apparatus for the controlled delivery or release of nicotine with a pressure sensitive adhesive nicotine reservoir with a uniform or irregular distribution of the nicotine, processes for the production thereof and the use thereof.

Nicotine-containing plasters, particularly for the purpose of stopping smoking are known. Thus, for example, DE-OS 34 38 284 (Tilly) describes a nicotine-containing depot plaster. It is proposed in "Drug and Alcohol Dependence" vol. 13, 1984, pp. 209-213 by J. E. Rose, N. E. Jarvic and K. D. Rose to supply nicotine transdermally to nicotine-dependent patients, in order to prevent habitual smokers, who are nicotine-dependent, from inhaling carcinogenic substances. Tests have been carried out with aqueous nicotine solutions, which were protected by means of a thin polyethylene coating from evaporating following application to the skin and it was found that nicotine permeates the skin and the same nicotine level as through smoking can be obtained by means of transdermal nicotine administration.

Etscorn proposes in U.S. Pat. No. 3,597,961 a simple nicotine plaster for the purpose of enabling people to stop smoking, in which the nicotine, which is present in a cavity in a plaster and optionally covered by a nicotine-permeable membrane, can be brought into contact with the skin, so as to permit the permeation of the nicotine into the human body and to combat nicotine dependence of smokers.

DE-OS 36 29 304 proposes a nicotine plaster using a nicotine depot in a nicotine-distributing acrylate matrix prepared from an acrylate solution, accompanied by the evaporation of the solvent.

Nicotine plasters are basically difficult to produce, because nicotine is very volatile and also toxic. The production of nicotine plaster components, particularly the components of the pressure sensitive adhesive matrix from the solution is disadvantageous for several reasons. It leads to high technical effort and costs for the handling of the solvent, whilst in addition it is necessary to use for medical purposes highly pure and therefore expensive solvents, in order to ensure a corresponding freedom from residues in the apparatus for the dissolving of the adhesive or its starting materials. Another problem is to achieve freedom from solvents in the apparatus and for this purpose expensive drying sections and suction plants are required. When processing nicotine the problem more particularly occurs that on evaporating the solvent a considerable proportion of the highly volatile nicotine can evaporate, which is highly undesirable due to the volatility and toxicity of nicotine. Thus, costs result from the use, recovery or separation of solvents and nicotine in order to avoid prejudicing the environment. In addition, the flammability of the solvent constitutes an additional risk. It is necessary to take complicated and costly protective measures for the safety of the working personnel.

The problem of the present invention is therefore to avoid the aforementioned disadvantages of the prior art apparatuses and processes.

According to the invention this problem is solved by an apparatus for the controlled delivery of nicotine, in which the reservoir is produced using a hot melt pressure sensitive adhesive with a processing temperature of 40° to 80° C., preferably 40° to 60° C. and in particularly preferred manner 40° to 55° C.

As a result of these measures the inventive apparatus can be produced at low temperature, without solvents and accompanied by a considerable saving on materials in a rapid manner and without time-consuming drying stages, accompanied by less prejudice to the environment, which inter alia leads to a much less expensive product.

An inventive process for the production of such a nicotine plaster comprises the continuous or discontinuous application of nicotine-containing, melted hot melt pressure sensitive adhesive at a temperature of the latter between 40° and 80°, preferably 40° and 60° and in particularly preferred manner 40° and 55° C. to a carrier and optionally applying the protective layer material.

A further inventive process comprises the continuous or discontinuous application of the nicotine-containing, melted hot melt pressure sensitive adhesive at a temperature of the latter between 40° and 80° C., preferably 40° and 60° C. and in particularly preferred manner 40° and 55° C. to a protective layer material and optionally applying a carrier.

The inventive apparatus can e.g. be used in human or veterinary medicine, particularly for the purpose of stopping smoking. It has also already been proposed to locally use fungicidal nicotine in plaster form for the control of fungal attacks to the skin. It can also be used as an apparatus for the release of nicotine as a respiratory, contact or stomach poison in pest control.

Advantageous further developments of the invention can be gathered from the subclaims.

The term hot melt contact adhesive is understood to mean any pressure sensitive adhesive, which is adequately liquid when hot, so that it can be applied without difficulty at temperatures above 40° C.

As inventively usable hot melt pressure sensitive adhesives can inter alia be used those which are known to the Expert and such as are inter alia described in DE-OS 15 94 268 (SUN OIL CO.), DE-OS 24 13 979 (E.I. DU PONT DE NEMOURS), DE-OS 24 35 863 (DYNAMIT NOBEL AG), DE-OS 28 00 302 (CIBA GEIGY), EP-A-104 005 (PERSONAL PRODUCTS CO.), JP 6104 2583 and JP 61 281 810, EP-OS 131 460 (EXXON), EP-OS 234 856 (EXXON), EP-OS 185 992 (EASTMAN KODAK), as well as U.S. Pat. Nos. 3,699,963 and 4,358,557 (EASTMAN KODAK) and express reference is made to this prior art to avoid unnecessary repetition.

The basic polymers can be constituted e.g. by polyamides, polyesters, polycaprolactams, polycaprolactone, ethylene-vinyl acetate copolymers (EVA), ethylene-ethylacrylate copolymers (EEA), polyvinylethers, polyacrylate esters, polyvinylacetals, polyvinylacetates, styrene-butadiene block polymers, isoprene block polymers, polyurethanes, ethylcellulose, cellulose acetate-butyrate, synthetic rubbers (e.g. neoprene rubber), polyisobutylene, butyl rubber, acrylonitrile-butadiene, copolymers, epoxy resins, melamine resins, phenol-formaldehyde resins and resorcinol-formaldehyde resins and inter alia the following modifying resins can be used: hydrogenated colophony, polymerized colophony, dimerized resin acids, disproportionated colophony, colophony methyl esters, hydrogenated colophony glycerol esters, hydrogenated colophony methyl esters, pentalesters, hydrogenated colophony triethyleneglycolesters, hydroabiethyl alcohol and its derivatives, glycerol esters ditriolesters and pentaesters of resin acids, polymerized colophony pentalesters, dimerized colophony pentalesters, dimerized colophony glycerol esters, esters of maleic acid or phenol-modified colophony, aromatic and aliphatic hydrocarbon resins, hydrogenated resins, polyterpene resins, modified terpene resins, waxes, low molecular weight polyethylene and polypropylene and alkyl-styrene copolymers. To these resins can optionally be added plasticizers, such as e.g. adipic acid esters, phosphoric acid esters, phthalic acid esters, polyesters, fatty acid esters, citric acid esters or epoxide plasticizers. It is also possible to admix stabilizers, such as tocopherol, substituted phenols, hydroquinones, pyrocatechols, aromatic amines and optionally also fillers, such as e.g. titanium dioxide, magnesium oxide, zinc oxide and silicon dioxide.

Typical compositions for hot pressure sensitive contact adhesives to be used are those prepared from between 10 and 100% by weight, preferably 20 to 80% by weight and in particularly preferred manner 20 to 50% by weight of polymer, between 10 and 80% by weight, preferably 15 to 60% by weight of plasticizer, between 10 and 80% by weight, preferably 15 to 60% by weight of tackifier, optionally 0.1 to 5% by weight of antiagers and optionally 0 to 70% by weight of fillers, the sum of the percentages of the components always being 100.

Preferably the hot melt pressure sensitive adhesive contains 10 to 50% by weight of styrene-isoprene-styrene synthetic rubber, such as is commercially available under the name CARIFLEX TR 1107 of SHELL, between 10 and 80% by weight of a hydrogenated alcohol, such as is commercially available under the name ABITOL from HERCULES, between 10 and 80% by weight of a hydrocarbon resin, e.g. HERCURES C from HERCULES, between 1 and 40% by weight of esters of vegetable fatty acids, e.g. MIGLYOL 812 of DYNAMIT NOBEL and optionally up to 5% by weight of antiagers, such as hydroquinone etc. as well as up to 70% by weight of fillers.

In a further preferred embodiment of the invention the hot melt pressure sensitive adhesive has 10 to 50% by weight of a polycaprolactone, e.g. CAPA 650 of INTEROX, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, such as MIGLYOL 812 of DYNAMIT NOBEL and optionally up to 5% by weight of antiagers, as well as up to 70% by weight of fillers.

It can be advantageous for the hot melt pressure sensitive adhesive to have 10 to 50% by weight of polyethylene-vinyl acetate, such as EVATANE 28-25 of ATOCHEM, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, such as hydroquinone, etc. and up to 70% by weight of fillers.

A suitable hot melt pressure sensitive adhesive can contain up to 10 to 50% by weight of polyurethane, such as e.g. LUPHEN P 1110 of BASF, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

It is also possible for the hot melt pressure sensitive adhesive to contain up to 10 to 50% by weight of polyamide, such as e.g. EURELON 930 of SCHERING, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

It is also possible to use a hot melt pressure sensitive adhesive with 10 to 50% by weight of epoxide, e.g. EUREPOX 7001 of SCHERING, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, such as hydroquinone, etc., as well as up to 70% by weight of fillers.

Another hot melt pressure sensitive adhesive usable in the production of inventive transdermal systems has up to 10 to 50% by weight of polyisobutene with a tacky, rubber-like consistency, such as e.g. OPPANOL B 50 of BASF, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

It is finally preferred to use hot melt pressure sensitive adhesives with a polyester base and which e.g. contain between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

Inventive apparatuses can also have one or more substance depots, where the substance is present in a higher concentration than the active substance-possessing hot melt pressure sensitive adhesive layer, so that higher substance doses can be processed and consequently the apparatus can remain in use for a longer period before it has to be replaced. Typical constructions appear e.g. in DE-OS 36 29 304. Preferred constructions of the invention appear in the subclaims, to which reference is hereby expressly made.

The formation of the components of the apparatus having hot melt pressure sensitive adhesives with a processing temperature between 40° and 80° C., can take place by extrusion, pouring, roller application, knife coating, spraying or a pressing process.

A limit value for the processability of the hot melt pressure sensitive adhesive in many of these processes occurs at a viscosity of approximately 80,000 Pa.

If the substrate to be treated with the adhesive, a component of the apparatus, could be damaged by the temperature of the hot-applied adhesive, either through decomposition, reaction or partial melting, use can be made of a cooled substrate. Cooling can take place by a per se known process, such as through the introduction of cold inert gases or contacting with a cooling surface.

The hot melt pressure sensitive adhesive can e.g. be applied in layer form or in individual areas, corresponding to a predetermined pattern, to the protective layer or the covering material.

When using the highly volatile and toxic nicotine, the following measures are appropriate for processing purposes:
A. working at temperatures which are as low as possible,
B. increasing the external pressure to reduce evaporation,
C. saturation of the vapour chamber over the melt with the vaporous substance and
D. working with the minimum quantity of volatile substance in the melt.

As a result of the toxicity of nicotine and its high volatility, process variants taking place in closed systems or encapsulated apparatuses are preferred. Obviously these measures, such as e.g. working in an encapsulated plant, are limited by the laws known to the Expert through the proposed use of the apparatus to be produced and also the material characteristics.

As no solvents have to be evaporated, the apparatus can be covered with the carrier or protective layer material immediately following the application of the heated hot melt pressure sensitive adhesive, so that further evaporation of the nicotine can be prevented.

As a result of the inventive process, there is no longer any need to use solvent-containing, pressure sensitive adhesive materials in the processing of the highly volatile nicotine, which greatly increases safety of production, because now no toxic solvent residues can be left behind in the medicinal administration form, which leads to a much simpler application process and to considerable production cost savings.

BRIEF DESCRIPTION OF THE DRAWINGS

Further features and advantages of the invention are described in greater detail hereinafter relative to the drawings, wherein show.

DESCRIPTION OF PREFERRED EMBODIMENTS

Figure 1:
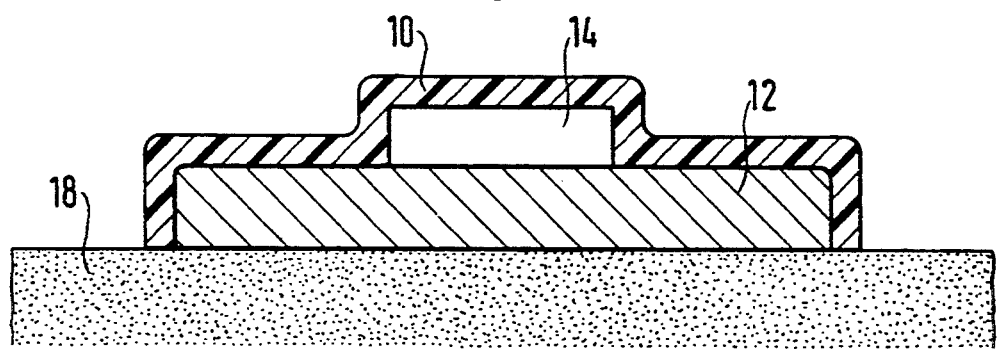
FIG. 1 a diagrammatically represented section through an inventive nicotine plaster with nicotine depot.

FIG. 1 shows a nicotine plaster with a nicotine depot 14, a hot melt pressure sensitive adhesive layer 12, as well as a nicotine-impermeable backing layer 10, on which the nicotine depot 14 rests and which is stuck to the skin 18. Nicotine now migrates continuously at a predetermined rate through the hot melt pressure sensitive adhesive layer 12 into the skin 18, so that the nicotine content in the hot melt pressure sensitive adhesive layer decreases. The nicotine decrease is compensated by the after-flow of nicotine from the nicotine depot 14, so that over a previously determined period of time there is an equilibrium concentration of the nicotine in the hot melt pressure sensitive adhesive 12, which ensures that a constant nicotine quantity is supplied to the skin 18.

It is assumed that the nicotine depot 14 contains highly concentrated nicotine, which can be e.g. absorbed on an inert carrier or a support material, such as a textile material.

Figure 2:
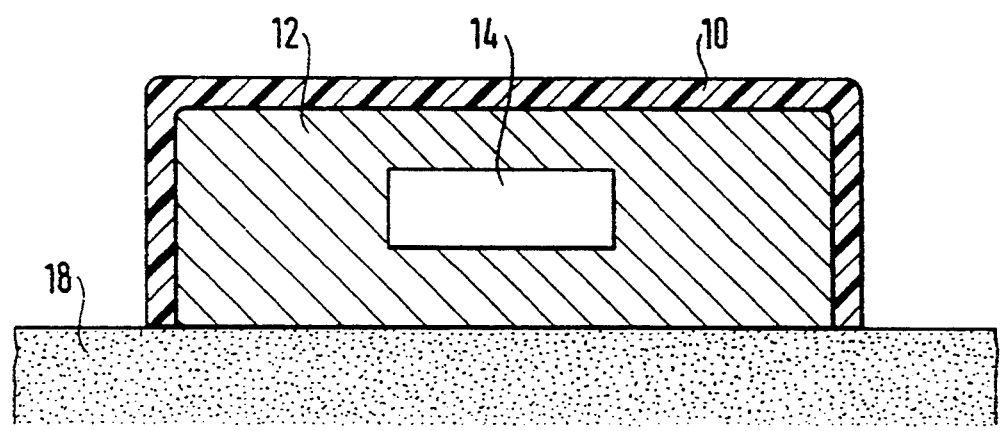
FIG. 2 diagrammatically a section through a further nicotine plaster with nicotine depot.

FIG. 2 shows another embodiment of an inventive apparatus, in which a nicotine depot 14 is surrounded on all sides by the hot melt pressure sensitive adhesive 12.

Figure 3:
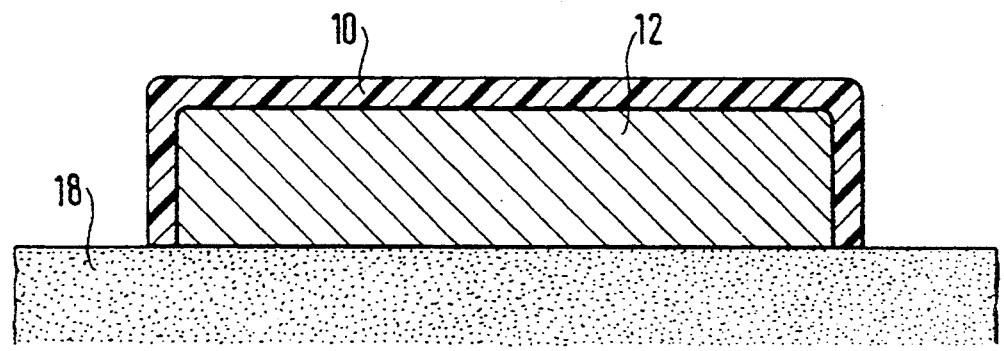
FIG. 3 a diagrammatically represented section through an inventive nicotine plaster without nicotine depot.

FIG. 3 shows another embodiment of an inventive nicotine plaster, in which a nicotine-containing hot melt pressure sensitive adhesive layer 12 is applied to an impermeable backing layer 10 in such a way that the latter covers the adhesive 12 on three sides. By means of the free hot melt pressure sensitive adhesive surface the plaster is stuck to the skin 18, so that a whole-area skin contact over the application period is ensured and the transfer of the nicotine to the skin always takes place over a constant surface at a constant speed, so that constant nicotine doses are delivered.

The inventively improved production of a nicotine plaster will now be described.

Firstly a mixture of nicotine and hot melt pressure sensitive adhesive is prepared. The mixture is then brought to the hot melt pressure sensitive adhesive processing temperature and is immediately applied from the melt to a nicotine-impermeable backing layer material. The further processing, such as the application of an adhesively finished protective layer material, takes place in the conventional way.

What is claimed is:

1. Process for the production of an apparatus for controlled transdermal release of nicotine having a hot melt pressure sensitive adhesive-nicotine reservoir in which there is a distribution of nicotine, said process comprising heating hot melt pressure sensitive adhesive to form a melt at a processing temperature of 40° to 80° C. under conditions to introduce nicotine into the melt, and applying the mixture from the melt to a carrier material, thereby to provide an apparatus for controlled transdermal delivery of nicotine.

2. Process according to claim 1, wherein the processing temperature of the hot melt pressure sensitive adhesive is between 40° and 60° C.

3. Process according to claim 1, wherein the processing temperature of the hot melt pressure sensitive adhesive is between 40° and 55° C.

4. Process according to claim 1, wherein the hot melt pressure sensitive adhesive is applied onto a basis formed of material selected from the group consisting of styrene-isoprene-styrene block polymers-polycaptolactones, ethylene-vinylacetate-copolymers, polyurethanes, polyepoxides, polyisobutenes, and polyvinylethers.

5. Process according to claim 4 wherein the basis further includes a material selected from the group consisting of plasticisers, tackifiers, fillers, anti-agers and thixotropic agents.

6. Process according to claim 1, wherein the hot melt pressure sensitive adhesive is produced from between 10 and 80% by weight of polymer, between 10 to 80% by weight of plasticiser, and between 10 and 80% by weight of tackifier, whereas the sum of percentages is always 100.

7. Process according to claim 6, wherein the hot melt pressure sensitive adhesive includes between 20 and 80% by weight of polymer.

8. Process according to claim 6, wherein the hot melt pressure sensitive adhesive includes between 20 and 50% by weight of polymer.

9. Process according to claim 6, wherein the hot melt pressure sensitive adhesive is produced having 15 to 60% by weight of plasticiser.

10. Process according to claim 6, wherein the hot melt pressure sensitive adhesive includes 15 to 60% by weight of tackifier.

11. Process according to claim 6, wherein the hot melt pressure sensitive adhesive includes 0.1 to 5% by weight anti-agers.

12. Process according to claim 6, wherein the hot melt pressure sensitive adhesive includes 0 to 70% by weight of fillers.

13. Process according to claim 1, wherein nicotine containing melted hot melt pressure sensitive adhesive of between 40° and 80° C. is applied onto a protective layer material.

14. Process according to claim 13, wherein the nicotine containing hot melt pressure sensitive adhesive is applied at a temperature thereof between 40° and 60° C.

15. Process according to claim 13, wherein the nicotine containing hot melt pressure sensitive adhesive is applied at a temperature thereof between 40° to 55° C.

16. Process according to claim 13, in which the carrier material acts to cover the apparatus.

17. Process for the production of an apparatus according to claim 1, characterized by continuous or discontinuous application of nicotine containing melted hot melt pressure sensitive adhesive at a temperature of the hot melt pressure sensitive adhesive between 40° and 80° C. onto a protective layer material.

18. Process according to claim 17, wherein the melted hot melt pressure sensitive adhesive is at a temperature between 40° and 60° C.

19. Process according to claim 17, wherein the melted hot melt pressure sensitive adhesive is at a temperature between 40° and 55° C.

20. Process according the claim 17, in which the carrier material acts to cover the apparatus.

21. Process for the production of an apparatus according to claim 13, wherein the formation of the components of the apparatus that contain hot melt pressure sensitive adhesive with a processing temperature of between 40° and 80° C. is by a method selected from the group consisting of extrusion, pouring, roller application, knife coating, spraying, and pressing.

22. Apparatus for the controlled release of nicotine comprising a back side and a skin side,
wherein a pressure sensitive adhesive is on the skin side to adhere the apparatus to the skin;
wherein the nicotine is distributed through the pressure sensitive adhesive to the skin;
wherein the back side is impermeable to nicotine;
wherein the pressure sensitive adhesive is a hot melt adhesive which is liquid at a temperature of 40° to 80° C. and is applied without difficulty; and
wherein no additional adhesive besides the hot melt pressure sensitive adhesive is used to adhere the apparatus to the skin.

23. Apparatus according to claim 22, wherein the hot melt pressure sensitive adhesive having a distribution of nicotine comprises at least one layer thereof.

24. Apparatus according to claim 22, and further comprising a detachable protective layer.

25. The method of stopping people from smoking comprising using in human medicine an apparatus produced according to claim 1.

26. The method of controlling pests in veterinary medicine comprising using an apparatus produced according to claim 1 as a respiratory, contact or stomach poison.

27. Process according to claim 1, wherein the carrier material is the backing material and is nicotine-impermeable.

28. Process for the production of an apparatus for controlled transdermal release of nicotine having a hot melt pressure sensitive adhesive-nicotine reservoir in which there is a distribution of nicotine, said process comprising producing the reservoir by forming a mixture of nicotine and hot melt pressure sensitive adhesive, heating the mixture to form a melt at a processing temperature of 40° to 80° C., and applying the mixture from the melt to a backing material, thereby to provide an apparatus for constant transdermal delivery of nicotine.

29. Apparatus for the controlled release of nicotine comprising a back side and a skin side, wherein a pressure sensitive adhesive is on the skin side to adhere the apparatus to the skin;
wherein the nicotine is distributed through the pressure sensitive adhesive to the skin;
wherein the back side is impermeable to nicotine;
wherein the pressure sensitive adhesive is a hot melt adhesive; and
wherein no additional source of adhesive besides the hot melt pressure sensitive adhesive is used to adhere the apparatus to the skin.

* * * * *